US009505838B2

(12) United States Patent
Allan et al.

(10) Patent No.: US 9,505,838 B2
(45) Date of Patent: Nov. 29, 2016

(54) METHOD TO TREAT MIGRAINES USING CGRP ANTIBODIES

(71) Applicant: Eli Lilly and Company, Indianapolis, IN (US)

(72) Inventors: Barrett Allan, Encinitas, CA (US); Robert Jan Benschop, Indianapolis, IN (US); Mark Geoffrey Chambers, Zionsville, IN (US); Ryan James Darling, Fortville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 75 days.

(21) Appl. No.: 14/730,270

(22) Filed: Jun. 4, 2015

(65) Prior Publication Data

US 2015/0259415 A1  Sep. 17, 2015

Related U.S. Application Data

(62) Division of application No. 13/154,538, filed on Jun. 7, 2011, now Pat. No. 9,073,991.

(60) Provisional application No. 61/353,323, filed on Jun. 10, 2010.

(51) Int. Cl.
| | | |
|---|---|---|
| *G01N 33/53* | (2006.01) | |
| *A61K 39/395* | (2006.01) | |
| *C07K 16/26* | (2006.01) | |
| *A61K 39/00* | (2006.01) | |

(52) U.S. Cl.
CPC ......... *C07K 16/26* (2013.01); *A61K 2039/505* (2013.01); *A61K 2039/54* (2013.01); *C07K 2317/14* (2013.01); *C07K 2317/24* (2013.01); *C07K 2317/56* (2013.01); *C07K 2317/76* (2013.01); *C07K 2317/92* (2013.01)

(58) Field of Classification Search
CPC .................. A61K 2300/00; A61K 2039/505; A61K 38/57; A61K 45/06; A61K 38/225; A61K 2121/00; A61K 2123/00; A61K 38/00; A61K 39/00; C07K 2317/76; C07K 2317/56; C07K 2317/92; C07K 2317/565; C07K 16/18; C07K 2317/24; C07K 2317/55; C07K 2316/96; C07K 16/00; G01N 33/6896; G01N 2800/2842; G01N 2333/5753; G01N 33/5058; C12N 2320/30; C12P 21/00
See application file for complete search history.

(56) References Cited

U.S. PATENT DOCUMENTS

| | | |
|---|---|---|
| 2006/0228367 A1 | 10/2006 | Ulbrandt et al. |
| 2007/0041978 A1 | 2/2007 | Hattori et al. |
| 2009/0220489 A1 | 9/2009 | Zeller et al. |

FOREIGN PATENT DOCUMENTS

| | | |
|---|---|---|
| WO | 2007054809 A3 | 5/2007 |
| WO | 2007076336 A1 | 7/2007 |
| WO | 2009109908 A1 | 9/2009 |

OTHER PUBLICATIONS

Elvidge, Nat. Biotechnol. 2014; 32:707.*
Peroutka BioDrugs, 2014; 28: 237-244.*
Wang et al. Adv. Drug Delivery Rev. 2003. 55:949-965.*
Averbeck, "Osteoarthritic Mice Exhibit Enhanced Prostaglandin E2 and Unchanged Calcitonin Gene-Related Peptide Release in a Novel Isolated Knee Joint Model", The Journal of Rheumatology, 2004, pp. 2013-2020, vol. 31 (10).
Fernihough, "Regulation of calcitonin gene-related peptide and TRPV1 in a rat model of osteoarthritis", Neuroscience Letters, 2005, pp. 75-80, vol. 388.
Hernanz, "Effect of calcitonin gene-related peptide, neuropeptide Y, substance P, and vasoactive intestinal peptide on interleukin-1Beta, interleukin-6 and tumor necrosis factor-alpha production by peripheral whole blood cells from rheumatoid arthritis and osteoarthritis patients", Regulatory Peptides, 2003, pp. 19-24, vol. 115.
Hubbard, "Identification of the epitopes of calcitonin gene-related peptide (CGRP) for two anti-CGRP monoclonal antibodies by 2D NMR", Protein Science, 1997, pp. 1945-1952, vol. 6.
Karimian, "Plasma protein extravasation into the rat knee joint induced by calcitonin gene-related peptide", Neuroscience Letters, 1994, pp. 39-42, vol. 166.
Louis, "Immunization with Calcitonin Gene-Related Peptide Reduces the Inflammatory Response to Adjuvant Arthritis in the Rat", Neuroscience, 1990, pp. 727-731, vol. 39(3).
Mapp, "Substance P-, Calcitonin Gene-Related Peptide-and C-Flanking Peptide of Neuropeptide Y-Immunoreactive Fibres are present in Normal Synovium but Depleted in Patients with Rheumatoid Arthritis", Neuroscience, 1990, pp. 143-153, vol. 37(1).
Saito, "Distribution of Neuropeptides in Synovium of the Knee with Osteoarthritis", Clinical Orthopaedics and Related Research, 2000, pp. 172-182, vol. 376.
Saxler, "Localization of SP- and CGRP-immunopositive nerve fibers in the hip joint of patients with painful osteoarthritis and of patients with painless failed total hip arthroplasties", European Journal of Pain, 2007 pp. 67-74, vol. 11.
Tan, "Calcitonin gene-related peptide as an endogenous vasodilator: immunoblockade studies in vivo with an anti-calcitonin gene-related peptide monoclonal antibody and its Fab' fragment", Clinical Science, 1995, pp. 565-573, vol. 89.
Wong, "Monoclonal Antibody to Rat Alpha-CGRP: Production, Characterization, and In Vivo Immunoneutralization Activity", Hybridoma, 1993, pp. 93-106, vol. 12(1).

(Continued)

*Primary Examiner* — Chang-Yu Wang
(74) *Attorney, Agent, or Firm* — Sanjay M. Jivraj

(57) ABSTRACT

The present invention provides human engineered calcitonin gene related peptide (CGRP) antibodies or antigen-binding fragment thereof. In addition, the present invention provides the use of the human engineered calcitonin gene related peptide (CGRP) antibodies or antigen-binding fragment thereof for the treatment of osteoarthritis pain.

7 Claims, No Drawings

(56) References Cited

OTHER PUBLICATIONS

Zeller, "CGRP funcation-blocking antibodies inhibit neurogenic vasodilatation without affecting heart rate or arterial blood pressure in the rat", British Journal of Pharmacology, 2008, pp. 1-11.
Zhang, "Arthritic calcitonin/alpha calcitonin gene-related peptide knockout mice have reduced nociceptive hypersensitivity", Pain, 2001, pp. 265-273, vol. 89.
Rudikoff et al. Proc. Nati. Acad. S d . USA 1982, p. 1979, vol. 79.
Dodick, "Initial Results for LY2951742, A new Investigation Medicine for Migraine Prevention", American Headache Society Abstract.
Benschop, "Development of a novel antibody to calcitonin gene-related peptide for the treatment of osteoarthritis-related pain", Osteoarthritis and Cartilage, 2014, pp. 578-585, vol. 22.
Bigal, "Safety, tolerability, and efficacy of TEV-48125 for preventive treatment of chronic migraine: a multicentre, randomised, double-blind, placebo-controlled, phase 2b study", The Lancet, 2015, pp. 1091-1099, vol. 14.
Bullock, "Peripheral Calcitonin Gene-Related Peptide Receptor Activation and Mechanical Sensitization of the Joint in Rat Models of Osteoarthritis Pain", Arthritis & Rheumatology, 2014, pp. 2188-2200, vol. 66.
Dodick, "Safety and efficacy of LY2951742, a monoclonoal antibody to calcitonin gene-related peptide, for the prevention of migraine: a phase 2, randomised, double-blind, placebo-controlled study", the Lancet, 2014, pp. 885-8891, vol. 13.
Dodick, "Safety and efficacy of ALD403, an antibody to calcitonin gene-related peptide, for the prevention of frequent episodic migraine: a randomised, double-blind, placebo-controlled, exploratory phase 2 trial", the Lancet, 2014, pp. 1100-1107, vol. 13.
Durham, "Calcitonin Gene-Related Peptide (CGRP) and Migraine", Headache, 2006, pp. S3-S8, vol. 46(Suppl 1).

* cited by examiner

```
                        SEQUENCE LISTING

<160> NUMBER OF SEQ ID NOS: 43

<210> SEQ ID NO 1
<211> LENGTH: 37
<212> TYPE: PRT
<213> ORGANISM: Artificial Sequence
<220> FEATURE:
<223> OTHER INFORMATION: Synthetic Construct

<400> SEQUENCE: 1

Ala Cys Asp Thr Ala Thr Cys Val Thr His Arg Leu Ala Gly Leu Leu
1               5                   10                  15

Ser Arg Ser Gly Gly Val Val Lys Asn Asn Phe Val Pro Thr Asn Val
            20                  25                  30

Gly Ser Lys Ala Phe
        35

<210> SEQ ID NO 2
<211> LENGTH: 37
<212> TYPE: PRT
<213> ORGANISM: Artificial Sequence
<220> FEATURE:
<223> OTHER INFORMATION: Synthetic Construct

<400> SEQUENCE: 2

Ala Cys Asn Thr Ala Thr Cys Val Thr His Arg Leu Ala Gly Leu Leu
1               5                   10                  15

Ser Arg Ser Gly Gly Met Val Lys Ser Asn Phe Val Pro Thr Asn Val
            20                  25                  30

Gly Ser Lys Ala Phe
        35

<210> SEQ ID NO 3
<211> LENGTH: 11
<212> TYPE: PRT
<213> ORGANISM: Artificial Sequence
<220> FEATURE:
<223> OTHER INFORMATION: Synthetic Construct

<400> SEQUENCE: 3

Arg Ala Ser Gln Asp Ile Asp Asn Tyr Leu Asn
1               5                   10

<210> SEQ ID NO 4
```

```
<211> LENGTH: 7
<212> TYPE: PRT
<213> ORGANISM: Artificial Sequence
<220> FEATURE:
<223> OTHER INFORMATION: Synthetic Construct

<400> SEQUENCE: 4

Tyr Thr Ser Glu Tyr His Ser
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic Construct

<400> SEQUENCE: 5

Gln Gln Gly Asp Ala Leu Pro Pro Thr
1               5

<210> SEQ ID NO 6
<211> LENGTH: 11
<212> TYPE: PRT
<213> ORGANISM: Artificial Sequence
<220> FEATURE:
<223> OTHER INFORMATION: Synthetic Construct

<400> SEQUENCE: 6

Arg Ala Ser Lys Asp Ile Ser Lys Tyr Leu Asn
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Synthetic Construct

<400> SEQUENCE: 7

Tyr Thr Ser Gly Tyr His Ser
1               5

<210> SEQ ID NO 8
<211> LENGTH: 11
<212> TYPE: PRT
<213> ORGANISM: Artificial Sequence
<220> FEATURE:
<223> OTHER INFORMATION: Synthetic Construct

<400> SEQUENCE: 8

Arg Ala Ser Arg Pro Ile Asp Lys Tyr Leu Asn
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Synthetic Construct

<400> SEQUENCE: 9

Arg Ala Ser Gln Asp Ile Asp Lys Tyr Leu Asn
1               5                   10

<210> SEQ ID NO 10
<211> LENGTH: 11
```

```
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa at position 4 is Gln, Arg or Lys
<220> FEATURE:
<221> NAME/KEY: MISC_FEATURE
<222> LOCATION: (5)..(5)
<223> OTHER INFORMATION: Xaa at position 5 is Asp or Pro
<220> FEATURE:
<221> NAME/KEY: MISC_FEATURE
<222> LOCATION: (7)..(7)
<223> OTHER INFORMATION: Xaa at position 7 is Asp or Ser
<220> FEATURE:
<221> NAME/KEY: MISC_FEATURE
<222> LOCATION: (8)..(8)
<223> OTHER INFORMATION: Xaa at position 8 is Asn or Lys

<400> SEQUENCE: 10

Arg Ala Ser Xaa Xaa Ile Xaa Xaa Tyr Leu Asn
1               5                   10

<210> SEQ ID NO 11
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa at position 4 is Gly or Glu

<400> SEQUENCE: 11

Tyr Thr Ser Xaa Tyr His Ser
1               5

<210> SEQ ID NO 12
<211> LENGTH: 10
<212> TYPE: PRT
<213> ORGANISM: Artificial Sequence
<220> FEATURE:
<223> OTHER INFORMATION: Synthetic Construct

<400> SEQUENCE: 12

Gly Tyr Thr Phe Gly Asn Tyr Trp Met Gln
1               5                   10

<210> SEQ ID NO 13
<211> LENGTH: 17
<212> TYPE: PRT
<213> ORGANISM: Artificial Sequence
<220> FEATURE:
<223> OTHER INFORMATION: Synthetic Construct

<400> SEQUENCE: 13

Ala Ile Tyr Glu Gly Thr Gly Asp Thr Arg Tyr Ile Gln Lys Phe Ala
1               5                   10                  15
Gly

<210> SEQ ID NO 14
<211> LENGTH: 10
<212> TYPE: PRT
<213> ORGANISM: Artificial Sequence
<220> FEATURE:
<223> OTHER INFORMATION: Synthetic Construct
```

```
<400> SEQUENCE: 14

Leu Ser Asp Tyr Val Ser Gly Phe Ser Tyr
1               5                   10

<210> SEQ ID NO 15
<211> LENGTH: 17
<212> TYPE: PRT
<213> ORGANISM: Artificial sequence
<220> FEATURE:
<223> OTHER INFORMATION: Synthetic Construct

<400> SEQUENCE: 15

Ala Ile Tyr Glu Gly Thr Gly Lys Thr Val Tyr Ile Gln Lys Phe Ala
1               5                   10                  15

Gly

<210> SEQ ID NO 16
<211> LENGTH: 17
<212> TYPE: PRT
<213> ORGANISM: Artificial Sequence
<220> FEATURE:
<223> OTHER INFORMATION: Synthetic Construct

<400> SEQUENCE: 16

Ala Ile Tyr Glu Gly Thr Gly Lys Thr Val Tyr Ile Gln Lys Phe Ala
1               5                   10                  15

Asp

<210> SEQ ID NO 17
<211> LENGTH: 107
<212> TYPE: PRT
<213> ORGANISM: Artificial Sequence
<220> FEATURE:
<223> OTHER INFORMATION: Synthetic Construct

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asp Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Glu Tyr His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asp Ala Leu Pro Pro
                85                  90                  95

Thr Phe Gly Gln Gly Thr Lys Leu Glu Ile Lys
            100                 105

<210> SEQ ID NO 18
<211> LENGTH: 107
<212> TYPE: PRT
<213> ORGANISM: Artificial Sequence
<220> FEATURE:
<223> OTHER INFORMATION: Synthetic Construct

<400> SEQUENCE: 18

Asp Ile Gln Met Thr Gln Ser Pro Ser Ser Leu Ser Ala Ser Val Gly
1               5                   10                  15
```

```
Asp Arg Val Thr Ile Thr Cys Arg Ala Ser Gln Asp Ile Asp Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Glu Tyr His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asp Ala Leu Pro Pro
                85                  90                  95

Thr Phe Gly Gln Gly Thr Lys Leu Glu Ile Lys
            100                 105
```

<210> SEQ ID NO 19
<211> LENGTH: 107
<212> TYPE: PRT
<213> ORGANISM: Artificial Sequence
<220> FEATURE:
<223> OTHER INFORMATION: Synthetic Construct

<400> SEQUENCE: 19

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Asp Ile Ser Lys Tyr
            20                  25                  30

Leu Asn Trp Tyr Gln Gln Lys Pro Gly Lys Ala Pro Lys Leu Leu Ile
        35                  40                  45

Tyr Tyr Thr Ser Gly Tyr His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asp Ala Leu Pro Pro
                85                  90                  95

Thr Phe Gly Gly Gly Thr Lys Val Glu Ile Lys
            100                 105
```

<210> SEQ ID NO 20
<211> LENGTH: 107
<212> TYPE: PRT
<213> ORGANISM: Artificial Sequence
<220> FEATURE:
<223> OTHER INFORMATION: Synthetic Construct

<400> SEQUENCE: 20

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Arg Pro Ile Asp Lys Tyr
            20                  25                  30

Leu Asn Trp Tyr Gln Gln Lys Pro Gly Lys Ala Pro Lys Leu Leu Ile
        35                  40                  45

Tyr Tyr Thr Ser Glu Tyr His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asp Ala Leu Pro Pro
                85                  90                  95

Thr Phe Gly Gln Gly Thr Lys Leu Glu Ile Lys
            100                 105
```

<210> SEQ ID NO 21
<211> LENGTH: 107
<212> TYPE: PRT
<213> ORGANISM: Artificial Sequence
<220> FEATURE:
<223> OTHER INFORMATION: Synthetic Construct

<400> SEQUENCE: 21

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asp Lys Tyr
            20                  25                  30

Leu Asn Trp Tyr Gln Gln Lys Pro Gly Lys Ala Pro Lys Leu Leu Ile
        35                  40                  45

Tyr Tyr Thr Ser Gly Tyr His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asp Ala Leu Pro Pro
                85                  90                  95

Thr Phe Gly Gly Gly Thr Lys Val Glu Ile Lys
            100                 105
```

<210> SEQ ID NO 22
<211> LENGTH: 119
<212> TYPE: PRT
<213> ORGANISM: Artificial Sequence
<220> FEATURE:
<223> OTHER INFORMATION: Synthetic Construct

<400> SEQUENCE: 22

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Gly Asn Tyr
            20                  25                  30

Trp Met Gln Trp Val Arg Gln Ala Pro Gly Gln Gly Leu Glu Trp Met
        35                  40                  45

Gly Ala Ile Tyr Glu Gly Thr Gly Asp Thr Arg Tyr Ile Gln Lys Phe
50                  55                  60

Ala Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Leu Ser Asp Tyr Val Ser Gly Phe Ser Tyr Trp Gly Gln Gly
            100                 105                 110

Thr Leu Val Thr Val Ser Ser
        115
```

<210> SEQ ID NO 23
<211> LENGTH: 119
<212> TYPE: PRT
<213> ORGANISM: Artificial Sequence
<220> FEATURE:
<223> OTHER INFORMATION: Synthetic Construct

<400> SEQUENCE: 23

```
Gln Val Gln Leu Val Gln Ser Gly Ala Glu Val Lys Lys Pro Gly Ala
1               5                   10                  15
```

Ser Val Lys Val Ser Cys Lys Ala Ser Gly Tyr Thr Phe Gly Asn Tyr
            20                  25                  30

Trp Met Gln Trp Val Arg Gln Ala Pro Gly Gln Gly Leu Glu Trp Met
        35                  40                  45

Gly Ala Ile Tyr Glu Gly Thr Gly Lys Thr Val Tyr Ile Gln Lys Phe
    50                  55                  60

Ala Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Leu Ser Asp Tyr Val Ser Gly Phe Ser Tyr Trp Gly Gln Gly
            100                 105                 110

Thr Leu Val Thr Val Ser Ser
            115

<210> SEQ ID NO 24
<211> LENGTH: 119
<212> TYPE: PRT
<213> ORGANISM: Artificial Sequence
<220> FEATURE:
<223> OTHER INFORMATION: Synthetic Construct

<400> SEQUENCE: 24

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Gly Asn Tyr
            20                  25                  30

Trp Met Gln Trp Val Arg Gln Ala Pro Gly Gln Gly Leu Glu Trp Met
        35                  40                  45

Gly Ala Ile Tyr Glu Gly Thr Gly Lys Thr Val Tyr Ile Gln Lys Phe
    50                  55                  60

Ala Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Ser Asp Tyr Val Ser Gly Phe Gly Tyr Trp Gly Gln Gly
            100                 105                 110

Thr Thr Val Thr Val Ser Ser
            115

<210> SEQ ID NO 25
<211> LENGTH: 119
<212> TYPE: PRT
<213> ORGANISM: Artificial Sequence
<220> FEATURE:
<223> OTHER INFORMATION: Synthetic Construct

<400> SEQUENCE: 25

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Gly Asn Tyr
            20                  25                  30

Trp Met Gln Trp Val Arg Gln Ala Pro Gly Gln Gly Leu Glu Trp Met
        35                  40                  45

Gly Ala Ile Tyr Glu Gly Thr Gly Lys Thr Val Tyr Ile Gln Lys Phe
    50                  55                  60

Ala Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Leu Ser Asp Tyr Val Ser Gly Phe Gly Tyr Trp Gly Gln Gly
            100                 105                 110

Thr Leu Val Thr Val Ser Ser
        115

<210> SEQ ID NO 26
<211> LENGTH: 119
<212> TYPE: PRT
<213> ORGANISM: Artificial Sequence
<220> FEATURE:
<223> OTHER INFORMATION: Synthetic Construct

<400> SEQUENCE: 26

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Gly Asn Tyr
            20                  25                  30

Trp Met Gln Trp Val Arg Gln Ala Pro Gly Gln Gly Leu Glu Trp Met
        35                  40                  45

Gly Ala Ile Tyr Glu Gly Thr Gly Lys Thr Val Tyr Ile Gln Lys Phe
    50                  55                  60

Ala Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Ser Asp Tyr Val Ser Gly Phe Gly Tyr Trp Gly Gln Gly
            100                 105                 110

Thr Thr Val Thr Val Ser Ser
        115

<210> SEQ ID NO 27
<211> LENGTH: 214
<212> TYPE: PRT
<213> ORGANISM: Artificial Sequence
<220> FEATURE:
<223> OTHER INFORMATION: Synthetic Construct

<400> SEQUENCE: 27

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asp Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Glu Tyr His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asp Ala Leu Pro Pro
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210

<210> SEQ ID NO 28
<211> LENGTH: 214
<212> TYPE: PRT
<213> ORGANISM: Artificial Sequence
<220> FEATURE:
<223> OTHER INFORMATION: Synthetic Construct

<400> SEQUENCE: 28

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asp Asn Tyr
                20                  25                  30

Leu Asn Trp Tyr Gln Gln Lys Pro Gly Lys Ala Pro Lys Leu Leu Ile
            35                  40                  45

Tyr Tyr Thr Ser Glu Tyr His Ser Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asp Ala Leu Pro Pro
                85                  90                  95

Thr Phe Gly Gln Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210

<210> SEQ ID NO 29
<211> LENGTH: 214
<212> TYPE: PRT
<213> ORGANISM: Artificial Sequence
<220> FEATURE:
<223> OTHER INFORMATION: Synthetic Construct

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Asp Ile Ser Lys Tyr
            20                  25                  30

Leu Asn Trp Tyr Gln Gln Lys Pro Gly Lys Ala Pro Lys Leu Leu Ile
        35                  40                  45

Tyr Tyr Thr Ser Gly Tyr His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asp Ala Leu Pro Pro
            85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 30
<211> LENGTH: 214
<212> TYPE: PRT
<213> ORGANISM: Artificial Sequence
<220> FEATURE:
<223> OTHER INFORMATION: Synthetic Construct

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Arg Ala Ser Arg Pro Ile Asp Lys Tyr
            20                  25                  30

Leu Asn Trp Tyr Gln Gln Lys Pro Gly Lys Ala Pro Lys Leu Leu Ile
        35                  40                  45

Tyr Tyr Thr Ser Glu Tyr His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asp Ala Leu Pro Pro
            85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 31
<211> LENGTH: 214
<212> TYPE: PRT
<213> ORGANISM: Artificial Sequence
<220> FEATURE:
<223> OTHER INFORMATION: Synthetic Construct

<400> SEQUENCE: 31

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asp Lys Tyr
                20                  25                  30

Leu Asn Trp Tyr Gln Gln Lys Pro Gly Lys Ala Pro Lys Leu Leu Ile
            35                  40                  45

Tyr Tyr Thr Ser Gly Tyr His Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asp Ala Leu Pro Pro
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 32
<211> LENGTH: 445
<212> TYPE: PRT
<213> ORGANISM: Artificial Sequence
<220> FEATURE:
<223> OTHER INFORMATION: Synthetic Construct

<400> SEQUENCE: 32

```
Gln Val Gln Leu Val Gln Ser Gly Ala Glu Val Lys Lys Pro Gly Ala
1               5                   10                  15
```

-continued

Ser Val Lys Val Ser Cys Lys Ala Ser Gly Tyr Thr Phe Gly Asn Tyr
        20                  25                  30

Trp Met Gln Trp Val Arg Gln Ala Pro Gly Gln Gly Leu Glu Trp Met
        35                  40                  45

Gly Ala Ile Tyr Glu Gly Thr Gly Asp Thr Arg Tyr Ile Gln Lys Phe
50                  55                  60

Ala Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Leu Ser Asp Tyr Val Ser Gly Phe Ser Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

```
Asn His Tyr Thr Gln Lys Ser Leu Ser Leu Ser Leu Gly
            435                 440                 445
```

<210> SEQ ID NO 33
<211> LENGTH: 445
<212> TYPE: PRT
<213> ORGANISM: Artificial Sequence
<220> FEATURE:
<223> OTHER INFORMATION: Synthetic Construct

<400> SEQUENCE: 33

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Gly Asn Tyr
            20                  25                  30

Trp Met Gln Trp Val Arg Gln Ala Pro Gly Gln Gly Leu Glu Trp Met
        35                  40                  45

Gly Ala Ile Tyr Glu Gly Thr Gly Lys Thr Val Tyr Ile Gln Lys Phe
    50                  55                  60

Ala Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Leu Ser Asp Tyr Val Ser Gly Phe Ser Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350
```

```
Ser Gln Glu Glu Met Thr Lys Asn Gln Val Ser Leu Thr Cys Leu Val
            355                 360                 365
Lys Gly Phe Tyr Pro Ser Asp Ile Ala Val Glu Trp Glu Ser Asn Gly
    370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Arg Leu Thr Val Asp Lys Ser Arg Trp
                405                 410                 415
Gln Glu Gly Asn Val Phe Ser Cys Ser Val Met His Glu Ala Leu His
            420                 425                 430
Asn His Tyr Thr Gln Lys Ser Leu Ser Leu Ser Leu Gly
            435                 440                 445

<210> SEQ ID NO 34
<211> LENGTH: 445
<212> TYPE: PRT
<213> ORGANISM: Artificial Sequence
<220> FEATURE:
<223> OTHER INFORMATION: Synthetic Construct

<400> SEQUENCE: 34

Gln Val Gln Leu Val Gln Ser Gly Ala Glu Val Lys Lys Pro Gly Ser
1               5                   10                  15
Ser Val Lys Val Ser Cys Lys Ala Ser Gly Tyr Thr Phe Gly Asn Tyr
            20                  25                  30
Trp Met Gln Trp Val Arg Gln Ala Pro Gly Gln Gly Leu Glu Trp Met
        35                  40                  45
Gly Ala Ile Tyr Glu Gly Thr Gly Lys Thr Val Tyr Ile Gln Lys Phe
    50                  55                  60
Ala Asp Arg Val Thr Ile Thr Ala Asp Lys Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Leu Ser Asp Tyr Val Ser Gly Phe Gly Tyr Trp Gly Gln Gly
            100                 105                 110
Thr Thr Val Thr Val Ser Ser Ala Ser Thr Lys Gly Pro Ser Val Phe
        115                 120                 125
Pro Leu Ala Pro Cys Ser Arg Ser Thr Ser Glu Ser Thr Ala Ala Leu
    130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Lys Thr Tyr Thr Cys Asn Val Asp His Lys Pro
        195                 200                 205
Ser Asn Thr Lys Val Asp Lys Arg Val Glu Ser Lys Tyr Gly Pro Pro
    210                 215                 220
Cys Pro Pro Cys Pro Ala Pro Glu Ala Ala Gly Gly Pro Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser Gln Glu Asp Pro Glu Val
            260                 265                 270
```

```
Gln Phe Asn Trp Tyr Val Asp Gly Val Glu Val His Asn Ala Lys Thr
                275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly
        435                 440                 445

<210> SEQ ID NO 35
<211> LENGTH: 445
<212> TYPE: PRT
<213> ORGANISM: Artificial Sequence
<220> FEATURE:
<223> OTHER INFORMATION: Synthetic Construct

<400> SEQUENCE: 35

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Gly Asn Tyr
                20                  25                  30

Trp Met Gln Trp Val Arg Gln Ala Pro Gly Gln Gly Leu Glu Trp Met
            35                  40                  45

Gly Ala Ile Tyr Glu Gly Thr Gly Lys Thr Val Tyr Ile Gln Lys Phe
        50                  55                  60

Ala Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Leu Ser Asp Tyr Val Ser Gly Phe Gly Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190
```

```
Ser Ser Leu Gly Thr Lys Thr Tyr Thr Cys Asn Val Asp His Lys Pro
            195                 200                 205

Ser Asn Thr Lys Val Asp Lys Arg Val Glu Ser Lys Tyr Gly Pro Pro
210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
                260                 265                 270

Gln Phe Asn Trp Tyr Val Asp Gly Val Glu Val His Asn Ala Lys Thr
            275                 280                 285

Lys Pro Arg Glu Glu Gln Phe Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly
        435                 440                 445

<210> SEQ ID NO 36
<211> LENGTH: 445
<212> TYPE: PRT
<213> ORGANISM: Artificial Sequence
<220> FEATURE:
<223> OTHER INFORMATION: Synthetic Construct

<400> SEQUENCE: 36

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Gly Asn Tyr
                20                  25                  30

Trp Met Gln Trp Val Arg Gln Ala Pro Gly Gln Gly Leu Glu Trp Met
            35                  40                  45

Gly Ala Ile Tyr Glu Gly Thr Gly Lys Thr Val Tyr Ile Gln Lys Phe
        50                  55                  60

Ala Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Ser Asp Tyr Val Ser Gly Phe Gly Tyr Trp Gly Gln Gly
            100                 105                 110
```

```
Thr Thr Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly
        435                 440                 445

<210> SEQ ID NO 37
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (8)..(8)
<223> OTHER INFORMATION: Xaa at position 8 is Lys or Asp
<220> FEATURE:
<221> NAME/KEY: MISC_FEATURE
<222> LOCATION: (10)..(10)
<223> OTHER INFORMATION: Xaa at position 10 is Val or Arg
<220> FEATURE:
```

```
<221> NAME/KEY: MISC_FEATURE
<222> LOCATION: (17)..(17)
<223> OTHER INFORMATION: Xaa at position 17 is Asp or Gly

<400> SEQUENCE: 37

Ala Ile Tyr Glu Gly Thr Gly Xaa Thr Xaa Tyr Ile Gln Lys Phe Ala
1               5                   10                  15

Xaa

<210> SEQ ID NO 38
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (9)..(9)
<223> OTHER INFORMATION: Xaa at position 9 is Gly or Ser

<400> SEQUENCE: 38

Leu Ser Asp Tyr Val Ser Gly Phe Xaa Tyr
1               5                   10

<210> SEQ ID NO 39
<211> LENGTH: 10
<212> TYPE: PRT
<213> ORGANISM: Artificial Sequence
<220> FEATURE:
<223> OTHER INFORMATION: Synthetic Construct

<400> SEQUENCE: 39

Leu Ser Asp Tyr Val Ser Gly Phe Gly Tyr
1               5                   10

<210> SEQ ID NO 40
<211> LENGTH: 107
<212> TYPE: PRT
<213> ORGANISM: Artificial Sequence
<220> FEATURE:
<223> OTHER INFORMATION: Synthetic Construct

<400> SEQUENCE: 40

Glu Ile Val Leu Thr Gln Ser Pro Ala Thr Leu Ser Leu Ser Pro Gly
1               5                   10                  15

Glu Arg Ala Thr Leu Ser Cys Lys Ala Ser Lys Arg Val Thr Thr Tyr
                20                  25                  30

Val Ser Trp Tyr Gln Gln Lys Pro Gly Gln Ala Pro Arg Leu Leu Ile
            35                  40                  45

Tyr Gly Ala Ser Asn Arg Tyr Leu Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Ser Gln Ser Tyr Asn Tyr Pro Tyr
                85                  90                  95

Thr Phe Gly Gln Gly Thr Lys Leu Glu Ile Lys
                100                 105

<210> SEQ ID NO 41
<211> LENGTH: 122
<212> TYPE: PRT
<213> ORGANISM: Artificial Sequence
<220> FEATURE:
<223> OTHER INFORMATION: Synthetic Construct
```

<400> SEQUENCE: 41

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Ile Ser Trp Val Arg Gln Ala Pro Gly Lys Gly Leu Glu Trp Val
        35                  40                  45

Ala Glu Ile Arg Ser Glu Ser Asp Ala Ser Ala Thr His Tyr Ala Glu
50                  55                  60

Ala Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Leu Ala Tyr Phe Asp Tyr Gly Leu Ala Ile Gln Asn Tyr Trp
            100                 105                 110

Gly Gln Gly Thr Leu Val Thr Val Ser Ser
            115                 120
```

<210> SEQ ID NO 42
<211> LENGTH: 107
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (27)..(27)
<223> OTHER INFORMATION: Xaa at position 27 is Gln, Lys, or Arg
<220> FEATURE:
<221> NAME/KEY: MISC_FEATURE
<222> LOCATION: (28)..(28)
<223> OTHER INFORMATION: Xaa at position 28 is Asp or Pro
<220> FEATURE:
<221> NAME/KEY: MISC_FEATURE
<222> LOCATION: (30)..(30)
<223> OTHER INFORMATION: Xaa at position 30 is Asp or Ser
<220> FEATURE:
<221> NAME/KEY: MISC_FEATURE
<222> LOCATION: (31)..(31)
<223> OTHER INFORMATION: Xaa at position 31 is Lys or Asn
<220> FEATURE:
<221> NAME/KEY: MISC_FEATURE
<222> LOCATION: (53)..(53)
<223> OTHER INFORMATION: Xaa at position 53 is Glu or Gly
<220> FEATURE:
<221> NAME/KEY: MISC_FEATURE
<222> LOCATION: (73)..(73)
<223> OTHER INFORMATION: Xaa at position 73 is Phe or Leu
<220> FEATURE:
<221> NAME/KEY: MISC_FEATURE
<222> LOCATION: (83)..(83)
<223> OTHER INFORMATION: Xaa at position 83 is Ile or Phe
<220> FEATURE:
<221> NAME/KEY: MISC_FEATURE
<222> LOCATION: (100)..(100)
<223> OTHER INFORMATION: Xaa at position 100 is Gln or Gly
<220> FEATURE:
<221> NAME/KEY: MISC_FEATURE
<222> LOCATION: (104)..(104)
<223> OTHER INFORMATION: Xaa at position 104 is Leu or Val

<400> SEQUENCE: 42

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Xaa Xaa Ile Xaa Xaa Tyr
            20                  25                  30
```

-continued

```
Leu Asn Trp Tyr Gln Gln Lys Pro Gly Lys Ala Pro Lys Leu Leu Ile
         35                  40                  45

Tyr Tyr Thr Ser Xaa Tyr His Ser Gly Val Pro Ser Arg Phe Ser Gly
 50                  55                  60

Ser Gly Ser Gly Thr Asp Phe Thr Xaa Thr Ile Ser Ser Leu Gln Pro
 65                  70                  75                  80

Glu Asp Xaa Ala Thr Tyr Tyr Cys Gln Gln Gly Asp Ala Leu Pro Pro
                 85                  90                  95

Thr Phe Gly Xaa Gly Thr Lys Xaa Glu Ile Lys
                100                 105

<210> SEQ ID NO 43
<211> LENGTH: 119
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (16)..(16)
<223> OTHER INFORMATION: Xaa at position 16 is Ala or Ser
<220> FEATURE:
<221> NAME/KEY: MISC_FEATURE
<222> LOCATION: (57)..(57)
<223> OTHER INFORMATION: Xaa at position 57 is Lys or Asp
<220> FEATURE:
<221> NAME/KEY: MISC_FEATURE
<222> LOCATION: (59)..(59)
<223> OTHER INFORMATION: Xaa at position 59 is Val or Arg
<220> FEATURE:
<221> NAME/KEY: MISC_FEATURE
<222> LOCATION: (66)..(66)
<223> OTHER INFORMATION: Xaa at position 66 is Gly or Asp
<220> FEATURE:
<221> NAME/KEY: MISC_FEATURE
<222> LOCATION: (70)..(70)
<223> OTHER INFORMATION: Xaa at position 70 is Met or Ile
<220> FEATURE:
<221> NAME/KEY: MISC_FEATURE
<222> LOCATION: (72)..(72)
<223> OTHER INFORMATION: Xaa at position 72 is Arg or Ala
<220> FEATURE:
<221> NAME/KEY: MISC_FEATURE
<222> LOCATION: (74)..(74)
<223> OTHER INFORMATION: Xaa at position 74 is Thr or Lys
<220> FEATURE:
<221> NAME/KEY: MISC_FEATURE
<222> LOCATION: (79)..(79)
<223> OTHER INFORMATION: Xaa at position 79 is Val or Ala
<220> FEATURE:
<221> NAME/KEY: MISC_FEATURE
<222> LOCATION: (107)..(107)
<223> OTHER INFORMATION: Xaa at position 107 is Gly or Ser
<220> FEATURE:
<221> NAME/KEY: MISC_FEATURE
<222> LOCATION: (114)..(114)
<223> OTHER INFORMATION: Xaa at position 114 is Leu or Thr

<400> SEQUENCE: 43

Gln Val Gln Leu Val Gln Ser Gly Ala Glu Val Lys Lys Pro Gly Xaa
  1               5                  10                  15

Ser Val Lys Val Ser Cys Lys Ala Ser Gly Tyr Thr Phe Gly Asn Tyr
                 20                  25                  30

Trp Met Gln Trp Val Arg Gln Ala Pro Gly Gln Gly Leu Glu Trp Met
             35                  40                  45

Gly Ala Ile Tyr Glu Gly Thr Gly Xaa Thr Xaa Tyr Ile Gln Lys Phe
     50                  55                  60

Ala Xaa Arg Val Thr Xaa Thr Xaa Asp Xaa Ser Thr Ser Thr Xaa Tyr
 65                  70                  75                  80
```

```
-continued

Met Glu Leu Ser Ser Leu Arg Ser Glu Asp Thr Ala Val Tyr Tyr Cys
                85              90                  95

Ala Arg Leu Ser Asp Tyr Val Ser Gly Phe Xaa Tyr Trp Gly Gln Gly
            100                 105             110

Thr Xaa Val Thr Val Ser Ser
        115
```

METHOD TO TREAT MIGRAINES USING CGRP ANTIBODIES

This application is a divisional of U.S. Pat. No. 9,073,991, filed Jun. 7, 2011, which claims benefit of U.S. Provisional Application Ser. No. 61/353,323, filed Jun. 10, 2010.

The present invention is in the field of medicine, particularly in the field of antibodies to calcitonin gene-related peptide (CGRP). More specifically, the invention relates to CGRP antibodies and the use of the CGRP antibodies for therapy of osteoarthritis pain or migraines Calcitonin gene related peptide (CGRP) is a 37 amino acid neuropeptide secreted by the nerves of the central and peripheral nervous systems. CGRP is widely distributed in sensory nerves, both in the peripheral and central nervous system and displays a large number of different biological activities. CGRP is reported to play a role. When released from trigeminal and other nerve fibers, CGRP is thought to mediate its biological responses by binding to specific cell surface receptors.

CGRP has been reported to play a role in migraines as CGRP is released upon stimulation of sensory nerves and has potent vasodilatory activity. The release of CGRP increases vascular permeability and subsequent plasma protein leakage (plasma protein extravasation) in tissues innervated by trigeminal nerve fibers upon stimulation of these fibers. In addition, studies have reported that infusion of CGRP in patients who suffer from migraines has resulted in migraine-like symptoms.

CGRP is also reported to play a role in osteoarthritis (OA). OA is a chronic condition that affects a large percentage of people worldwide. Pain in arthritis is characterized by hyperalgesia (overly sensitive to normally non-noxious stimuli) and spontaneous pain (pain at rest). Inflammation of the joint causes peripheral and central sensitization. In peripheral sensitization, the normally high-threshold CGRP-containing nociceptors begin to respond to light pressure associated with normal joint movement. CGRP acts as a local facilitator of inflammatory processes. This continued process eventually leads to central sensitization in the spinal cord such that neurons become responsive to stimulation of inflamed as well as non-inflamed tissue. In preclinical models of OA pain in the rat, an increase in the number of CGRP positive nerve fibers was observed, positively correlating with the amount of pain.

Current standard of care for OA pain consists of non-steroidal anti-inflammatory drugs (NSAIDs) and selective Cox-2 inhibitors. Over time, many patients will become insensitive to these treatments or are not able to tolerate the high doses needed for effective pain relief. Follow-up treatments consist of intra-articular injections (hyaluronan) or opiates. The final treatment is surgical total joint replacement. Many of these treatments have negative side effects, ranging from gastro-intestinal (NSAIDs) to cardiovascular (Cox-2 inhibitors), are cumbersome and/or not very efficacious (intra-articular injections), carry the risk for abuse (opiates), or are restricted to only 1 joint (intra-articular injections, surgery).

Although CGRP antibodies for treating migraines and for treating inflammation pain have been disclosed (migraines-WO 2007/076336 and WO 2007/054809; OA-see, Antibody G1 of WO2009/109908A1), there is still a need for alternatives. Preferably, the treatment alternative is safe and efficacious. More preferably, the alternative treatment for OA will provide long-lasting pain relief across multiple joints that is tolerable to patients without the risk for dependence and/or abuse.

The present invention provides a human engineered CGRP antibody comprising a light chain variable region (LCVR) and a heavy chain variable region (HCVR), wherein said LCVR comprises LCDR1, LCDR2, and LCDR3 amino acid sequences and HCVR comprises HCDR1, HCDR2, and HCDR3 amino acid sequences which are selected from the group consisting of:

a)
LCDR1 is RASQDIDNYLN (SEQ ID NO: 3),
LCDR2 is YTSEYHS (SEQ ID NO: 4),
LCDR3 is QQGDALPPT (SEQ ID NO: 5),
HCDR1 is GYTFGNYWMQ (SEQ ID NO: 12),
HCDR2 is AIYEGTGDTRYIQKFAG (SEQ ID NO: 13), and
HCDR3 is LSDYVSGFSY (SEQ ID NO: 14);

b)
LCDR1 is RASQDIDNYLN (SEQ ID NO: 3),
LCDR2 is YTSEYHS (SEQ ID NO: 4),
LCDR3 is QQGDALPPT (SEQ ID NO: 5),
HCDR1 is GYTFGNYWMQ (SEQ ID NO: 12),
HCDR2 is AIYEGTGKTVYIQKFAG (SEQ ID NO: 15), and
HCDR3 is LSDYVSGFSY (SEQ ID NO: 14);

c)
LCDR1 is RASKDISKYLN (SEQ ID NO: 6),
LCDR2 is YTSGYHS (SEQ ID NO: 7),
LCDR3 is QQGDALPPT (SEQ ID NO: 5),
HCDR1 is GYTFGNYWMQ (SEQ ID NO: 12),
HCDR2 is AIYEGTGKTVYIQKFAD (SEQ ID NO: 16), and
HCDR3 is LSDYVSGFGY (SEQ ID NO: 39);

d)
LCDR1 is RASRPIDKYLN (SEQ ID NO: 8),
LCDR2 is YTSEYHS (SEQ ID NO: 4),
LCDR3 is QQGDALPPT (SEQ ID NO: 5),
HCDR1 is GYTFGNYWMQ (SEQ ID NO: 12),
HCDR2 is AIYEGTGKTVYIQKFAG (SEQ ID NO: 15), and
HCDR3 is LSDYVSGFGY (SEQ ID NO: 39); and e)
LCDR1 is RASQDIDKYLN (SEQ ID NO: 9),
LCDR2 is YTSGYHS (SEQ ID NO: 7),
LCDR3 is QQGDALPPT (SEQ ID NO: 5),
HCDR1 is GYTFGNYWMQ (SEQ ID NO: 12),
HCDR2 is AIYEGTGKTVYIQKFAG (SEQ ID NO: 15), and
HCDR3 is LSDYVSGFGY (SEQ ID NO: 39), wherein the human engineered CGRP antibody binds to human CGRP.

The present invention provides a human engineered CGRP antibody comprising an LCVR and an HCVR wherein LCDR1 is SEQ ID NO: 3, LCDR2 is SEQ ID NO: 4, LCDR3 is SEQ ID NO: 5, HCDR1 is SEQ ID NO: 12, HCDR2 is SEQ ID NO: 13, and HCDR3 is SEQ ID NO: 14, wherein the human engineered CGRP antibody binds to human CGRP. The present invention provides a human engineered CGRP antibody or antigen-binding fragment thereof comprising an LCVR and an HCVR wherein LCDR1 is SEQ ID NO: 3, LCDR2 is SEQ ID NO: 4, LCDR3 is SEQ ID NO: 5, HCDR1 is SEQ ID NO: 12, HCDR2 is SEQ ID NO: 15, and HCDR3 is SEQ ID NO: 14, wherein the human engineered CGRP antibody binds to human CGRP. The present invention provides a human engineered CGRP antibody comprising an LCVR and an HCVR wherein LCDR1 is SEQ ID NO: 6, LCDR2 is SEQ ID NO: 7, LCDR3 is SEQ ID NO: 5, HCDR1 is SEQ ID NO: 12, HCDR2 is SEQ ID NO: 16, and HCDR3 is SEQ ID NO: 39, wherein the human engineered CGRP antibody binds to human CGRP. The present invention provides a human engineered CGRP antibody comprising an LCVR and an HCVR wherein LCDR1 is SEQ ID NO: 8, LCDR2 is SEQ ID NO: 4, LCDR3 is SEQ ID NO: 5, HCDR1 is SEQ ID NO: 12, HCDR2 is SEQ ID NO: 15, and HCDR3 is SEQ ID NO: 39, wherein the human engineered CGRP antibody binds to human CGRP. The present invention provides a human engineered CGRP antibody comprising an LCVR and an HCVR wherein LCDR1 is SEQ ID NO: 9, LCDR2 is SEQ ID NO: 7, LCDR3 is SEQ ID NO: 5, HCDR1 is SEQ ID NO: 12, HCDR2 is SEQ ID NO: 15, and HCDR3 is SEQ ID NO: 39, wherein the human engineered CGRP antibody binds to human CGRP.

The present invention provides a human engineered CGRP antibody comprising an LCVR and an HCVR wherein LCDR1 is RASX$_1$X$_2$IX$_3$X$_4$YLN (SEQ ID NO: 10), LCDR2 is YTSX$_5$YHS (SEQ ID NO: 11), LCDR3 is QQGDALPPT (SEQ ID NO: 5) and HCDR1 is GYTFGNYWMQ (SEQ ID NO:12), HCDR2 is AIYEGTGX$_6$TX$_7$YIQKFAX$_8$ (SEQ ID NO: 37), and HCDR3 is LSDYVSGFX$_9$Y (SEQ ID NO: 38), wherein X$_1$ is Q, R, or K; X$_2$ is D or P, X$_3$ is D or S, X$_4$ is N or K, X$_5$ is G or E, X$_6$ is K or D, X$_7$ is V or R, X$_8$ is D or G, and X$_9$ is G or S, wherein the antibody binds to human CGRP.

In another embodiment, the present invention provides a human engineered CGRP antibody comprising a light chain variable region (LCVR) and a heavy chain variable region (HCVR), wherein the LCVR comprises
DIQMTQSPSSLSASVGDRVTITCRASX$_1$X$_2$IX$_3$X$_4$YLNW YQQKPGKAPKLLIYYTSX$_5$
YHSGYPSRFSGSGSGTDFTX$_6$TISSLQPEDX$_7$ATYYCQ QGDALPPTFGX$_8$GTKX$_9$EIK wherein X$_1$ is Q, K, or R; X$_2$ is D or P; X$_3$ is D or S; X$_4$ is K or N; X$_5$ is E or G; X$_6$ is F or L; X$_7$ is I or F; X$_8$ is Q or G; and X$_9$ is L or V. (SEQ ID NO: 42)
and the HCVR comprises
QVQLVQSGAEVKKPGX$_1$SVKVSCKASGYTFGNYWM QWVRQAPGQGLEWMGAI
YEGTGX$_2$TX$_3$YIQKFAX$_4$RVTX$_5$TX$_6$DX$_7$STSTX$_8$YMEL SSLRSEDTAVYYCARLSDY
VSGFX$_9$YWGQGTX$_{10}$VTVSS, wherein X$_1$=A or S; X$_2$=K or D; X$_3$=V or R; X$_4$=G or D; X$_5$=M or I; X$_6$=R or A; X$_7$=T or K; X$_8$=V or A; X$_9$=G or S; and X$_{10}$=L or T. (SEQ ID NO: 43), wherein the antibody binds to human CGRP.

In another embodiment, the present invention provides a human engineered CGRP antibody comprising a light chain variable region (LCVR) and a heavy chain variable region (HCVR), wherein the LCVR and HCVR are amino acid sequences selected from the group consisting of:
a. LCVR is SEQ ID NO: 17 and HCVR is SEQ ID NO: 22;
b. LCVR is SEQ ID NO: 18 and HCVR is SEQ ID NO: 23;
c. LCVR is SEQ ID NO: 19 and HCVR is SEQ ID NO: 24;
d. LCVR is SEQ ID NO: 20 and HCVR is SEQ ID NO: 25; and
e. LCVR is SEQ ID NO: 21 and HCVR is SEQ ID NO: 26.

The present invention provides a human engineered CGRP antibody comprising a LCVR of SEQ ID NO: 17 and an HCVR of SEQ ID NO: 22. In a preferred embodiment, the present invention provides a human engineered CGRP antibody comprising a LCVR of SEQ ID NO: 18 and an HCVR of SEQ ID NO: 23. The present invention provides a human engineered CGRP antibody comprising a LCVR of SEQ ID NO: 19 and an HCVR of SEQ ID NO: 24. The present invention provides a human engineered CGRP antibody comprising a LCVR of SEQ ID NO: 20 and an HCVR of SEQ ID NO: 25. The present invention provides a human engineered CGRP antibody comprising a LCVR of SEQ ID NO: 21 and an HCVR of SEQ ID NO: 26.

The present invention also provides a human engineered CGRP antibody comprising a light chain (LC) and a heavy chain (HC), wherein the LC and HC amino acid sequences are selected from the group consisting of:
a) LC is SEQ ID NO: 27 and HC is SEQ ID NO: 32;
b) LC is SEQ ID NO: 28 and HC is SEQ ID NO: 33;
c) LC is SEQ ID NO: 29 and HC is SEQ ID NO: 34;
d) LC is SEQ ID NO: 30 and HC is SEQ ID NO: 35; and
e) LC is SEQ OD NO: 31 and HC is SEQ ID NO: 36.

In an embodiment, the human engineered CGRP antibody comprises an LC of SEQ ID NO: 27 and a HC of SEQ ID NO: 32. In another embodiment, the human engineered CGRP antibody comprises an LC of SEQ ID NO: 28 and an HC of SEQ ID NO: 33. In another embodiment, the human engineered CGRP antibody comprises an LC of SEQ ID NO: 29 and an HC of SEQ ID NO: 34. In another embodiment, the human engineered CGRP antibody comprises an LC of SEQ ID NO: 30 and an HC of SEQ ID NO: 35. In another embodiment, the human engineered CGRP antibody comprises an LC of SEQ ID NO: 31 and an HC of SEQ ID NO: 36. In an embodiment, the human engineered CGRP antibody comprises two light chains and two heavy chains wherein each LC amino acid sequence is SEQ ID NO: 27 and each HC amino acid sequence is SEQ ID NO: 32. In an embodiment, the human engineered CGRP antibody comprises two light chains and two heavy chains wherein each LC amino acid sequence is SEQ ID NO: 28 and each HC amino acid sequence is SEQ ID NO: 33. In an embodiment, the human engineered CGRP antibody comprises two light chains and two heavy chains wherein each LC amino acid sequence is SEQ ID NO: 29 and each HC amino acid sequence is SEQ ID NO: 34. In a embodiment, the human engineered CGRP antibody comprises two light chains and two heavy chains wherein each LC amino acid sequence is SEQ ID NO: 30 and each HC amino acid sequence is SEQ ID NO: 35. In an embodiment, the human engineered CGRP antibody comprises two light chains and two heavy chains wherein each LC amino acid sequence is SEQ ID NO: 31 and each HC amino acid sequence is SEQ ID NO: 36. The present invention also provides antigen-binding fragment of the antibodies described herein.

The present invention also provides human engineered CGRP antibodies which have an IC50<1.0 nM in an assay essentially as described in Example 4. In an embodiment, the present invention provides a human engineered CGRP antibody comprising an LCVR and an HCVR wherein LCDR1 is SEQ ID NO: 6, LCDR2 is SEQ ID NO: 7, LCDR3 is SEQ ID NO: 5, HCDR1 is SEQ ID NO: 12, HCDR2 is SEQ ID NO: 16, and HCDR3 is SEQ ID NO: 39, and wherein the human engineered CGRP antibody binds to human CGRP and also has an IC50<1.0 nM in an assay essentially as described in Example 4. In an embodiment, the present invention provides a human engineered CGRP antibody comprising a LCVR amino acid sequence of SEQ ID NO: 19 and an HCVR amino acid sequence of SEQ ID NO: 24, wherein the human engineered CGRP antibody has an IC50<1.0 nM in an assay essentially as described Example 4. In an embodiment, the present invention provides a human engineered CGRP antibody comprising a LC amino acid sequence of SEQ ID NO: 29 and a HC amino acid sequence of SEQ ID NO: 34, wherein the human engineered CGRP antibody has an IC50<1.0 nM in an assay essentially as described in Example 4.

The present invention also provides human engineered CGRP antibodies which have an IC50<0.5 nM in an assay essentially as described in Example 4. In an embodiment, the present invention provides a human engineered CGRP antibody comprising an LCVR and an HCVR wherein LCDR1 is SEQ ID NO: 6, LCDR2 is SEQ ID NO: 7, LCDR3 is SEQ ID NO: 5, HCDR1 is SEQ ID NO: 12, HCDR2 is SEQ ID NO: 16, and HCDR3 is SEQ ID NO: 39, and wherein the human engineered CGRP antibody binds to human CGRP and also has an IC50<0.5 nM nM in an assay essentially as described in Example 4. In an embodiment, the present invention provides a human engineered CGRP antibody comprising a LCVR amino acid sequence of SEQ ID NO: 19 and an HCVR amino acid sequence of SEQ ID NO: 24, wherein the human engineered CGRP antibody has an IC50<0.5 nM nM in an assay essentially as described Example 4. In an embodiment, the present invention provides a human engineered CGRP antibody comprising a LC amino acid sequence of SEQ ID NO: 29 and a HC amino acid sequence of SEQ ID NO: 34, wherein the human engineered CGRP antibody has an IC50<0.5 nM nM in an assay essentially as described in Example 4.

The present invention also provides a pharmaceutical composition comprising a human engineered CGRP antibody or antigen-binding fragment thereof of the present invention and a pharmaceutically acceptable carrier, diluent or excipient. The present invention further provides a pharmaceutical composition comprising a CGRP antibody of the present invention together with a pharmaceutically acceptable carrier and optionally, other therapeutic ingredients.

In a further aspect, the present invention provides a method of treating osteoarthritis pain comprising administering to a patient in need thereof a human engineered CGRP antibody or antigen-binding fragment thereof of the present invention. In another aspect, the present invention provides a method of treating migraines comprising administering to a patient in need thereof a human engineered CGRP antibody or antigen-binding fragment thereof of the present invention The present invention also provides a human engineered CGRP antibody or antigen-binding fragment thereof of the present invention for use in therapy. In another aspect, the present invention provides a human engineered CGRP antibody or antigen-binding fragment thereof of the present invention for the treatment of osteoarthritis pain. In a further aspect, the present invention provides a human engineered CGRP antibody or antigen-binding fragment thereof of the present invention for the treatment of migraines.

The present invention also provides the use of a human engineered CGRP antibody or antigen-binding fragment thereof of the present invention for use in the treatment of osteoarthritis pain. In another aspect, the present invention also provides the use of a human engineered CGRP antibody or antigen-binding fragment thereof of the present invention for use in the treatment of migraines. The present invention also provides the use of a human engineered CGRP antibody or antigen binding fragment thereof in the manufacture of a medicament for the treatment of osteoarthritis. The present invention also provides the use of a human engineered CGRP antibody or antigen binding fragment thereof in the manufacture of a medicament for the treatment of migraines.

A full-length antibody as it exists naturally is an immunoglobulin molecule comprising 2 heavy (H) chains and 2 light (L) chains interconnected by disulfide bonds. The amino terminal portion of each chain includes a variable region of about 100-110 amino acids primarily responsible for antigen recognition via the complementarity determining regions (CDRs) contained therein. The carboxy-terminal portion of each chain defines a constant region primarily responsible for effector function.

The CDRs are interspersed with regions that are more conserved, termed framework regions (FR). Each light chain variable region (LCVR) and heavy chain variable region (HCVR) is composed of 3 CDRs and 4 FRs, arranged from amino-terminus to carboxy-terminus in the following order: FR1, CDR1, FR2, CDR2, FR3, CDR3, FR4. The 3 CDRs of the light chain are referred to as "LCDR1, LCDR2, and LCDR3" and the 3 CDRs of the heavy chain are referred to as "HCDR1, HCDR2, and HCDR3." The CDRs contain most of the residues which form specific interactions with the antigen. The numbering and positioning of CDR amino acid residues within the LCVR and HCVR regions is in accordance with the well-known Kabat numbering convention.

Light chains are classified as kappa or lambda, and are characterized by a particular constant region as known in the art. Heavy chains are classified as gamma, mu, alpha, delta, or epsilon, and define the isotype of an antibody as IgG, IgM, IgA, IgD, or IgE, respectively. IgG antibodies can be further divided into subclasses, e.g., IgG1, IgG2, IgG3, IgG4. Each heavy chain type is characterized by a particular constant region with a sequence well known in the art.

As used herein, the term "monoclonal antibody" (Mab) refers to an antibody that is derived from a single copy or clone including, for example, any eukaryotic, prokaryotic, or phage clone, and not the method by which it is produced. Mabs of the present invention preferably exist in a homogeneous or substantially homogeneous population. Complete Mabs contain 2 heavy chains and 2 light chains. "Antigen-binding fragments" of such monoclonal antibodies include, for example, Fab fragments, Fab' fragments, F(ab')$_2$ fragments, and single chain Fv fragments. Monoclonal antibodies and antigen-binding fragments thereof of the present invention can be produced, for example, by recombinant technologies, phage display technologies, synthetic technologies, e.g., CDR-grafting, or combinations of such technologies, or other technologies known in the art. For example, mice can be immunized with human CGRP or fragments thereof, the resulting antibodies can be recovered and purified, and determination of whether they possess binding and functional properties similar to or the same as the antibody compounds disclosed herein can be assessed by the methods disclosed in Examples below. Antigen-binding fragments can also be prepared by conventional methods. Methods for producing and purifying antibodies and antigen-binding fragments are well known in the art and can be found, for example, in Harlow and Lane (1988) *Antibodies, A Laboratory Manual*, Cold Spring Harbor Laboratory Press, Cold Spring Harbor, N.Y., chapters 5-8 and 15, ISBN 0-87969-314-2.

The phrase "human engineered CGRP antibodies" refers to monoclonal antibodies created and/or manipulated to have binding and functional properties according to the invention, bind to human CGRP, and that have framework regions that are substantially human or fully human surrounding CDRs derived from a non-human antibody. "Antigen-binding fragments" of such human engineered antibodies include, for example, Fab fragments, Fab' fragments, F(ab')$_2$ fragments, and single chain Fv fragments. "Framework region" or "framework sequence" refers to any one of framework regions 1 to 4. Human engineered antibodies and antigen-binding fragments thereof encompassed by the present invention include molecules wherein any one or more of framework regions 1 to 4 is substantially or fully human, i.e., wherein any of the possible combinations of individual substantially or fully human framework regions 1 to 4, is present. For example, this includes molecules in which framework region 1 and framework region 2, framework region 1 and framework region 3, framework region 1, 2, and 3, etc., are substantially or fully human. Substantially human frameworks are those that have at least about 80% sequence identity to a known human germline framework sequence. Preferably, the substantially human frameworks have at least about 85%, about 90%, about 95%, or about 99% sequence identity to a known human germline framework sequence.

Fully human frameworks are those that are identical to a known human germline framework sequence. Human framework germline sequences can be obtained from ImMunoGeneTics (IMGT) or from *The Immuno globulin Facts-Book* by Marie-Paule Lefranc and Gerard Lefranc, Academic Press, 2001, ISBN 012441351. For example, germline light chain frameworks can be selected from the group consisting of: A11, A17, A18, A19, A20, A27, A30, L1, L11, L12, L2, L5, L15, L6, L8, O12, O2, and O8, and germline heavy chain framework regions can be selected from the group consisting of: VH2-5, VH2-26, VH2-70, VH3-20, VH3-72, VHI-46, VH3-9, VH3-66, VH3-74, VH4-31, VHI-18, VHI-69, VI-13-7, VH3-11, VH3-15, VH3-21, VH3-23, VH3-30, VH3-48, VH4-39, VH4-59, and VH5-51.

Human engineered antibodies in addition to those disclosed herein exhibiting similar functional properties according to the present invention can be generated using several different methods. The specific antibody compounds disclosed herein can be used as templates or parent antibody compounds to prepare additional antibody compounds. In one approach, the parent antibody compound CDRs are grafted into a human framework that has a high sequence identity with the parent antibody compound framework. The sequence identity of the new framework will generally be at least about 80%, at least about 85%, at least about 90%, at least about 95%, or at least about 99% identical to the sequence of the corresponding framework in the parent antibody compound. This grafting may result in a reduction in binding affinity compared to that of the parent antibody. If this is the case, the framework can be back-mutated to the parent framework at certain positions based on specific criteria disclosed by Queen et al. (1991) *Proc. Natl. Acad. Sci. USA* 88:2869. Additional references describing methods useful in humanizing mouse antibodies include U.S. Pat. Nos. 4,816,397; 5,225,539, and 5,693,761; computer programs ABMOD and ENCAD as described in Levitt (1983) *J. Mol. Biol.* 168:595-620; and the method of Winter and co-workers (Jones et al. (1986) *Nature* 321:522-525; Riechmann et al. (1988) *Nature* 332:323-327; and Verhoeyen et al. (1988) *Science* 239:1534-1536.

The identification of residues to consider for back-mutation can be carried out as follows:

When an amino acid falls under the following category, the framework amino acid of the human germ-line sequence that is being used (the "acceptor framework") is replaced by a framework amino acid from a framework of the parent antibody compound (the "donor framework"):

(a) the amino acid in the human framework region of the acceptor framework is unusual for human frameworks at that position, whereas the corresponding amino acid in the donor immunoglobulin is typical for human frameworks at that position;

(b) the position of the amino acid is immediately adjacent to one of the CDRs; or (c) any side chain atom of a framework amino acid is within about 5-6 angstroms (center-to-center) of any atom of a CDR amino acid in a three dimensional immunoglobulin model.

When each of the amino acids in the human framework region of the acceptor framework and a corresponding amino acid in the donor framework is generally unusual for human frameworks at that position, such amino acid can be replaced by an amino acid typical for human frameworks at that position. This back-mutation criterion enables one to recover the activity of the parent antibody compound.

Another approach to generating human engineered antibodies exhibiting similar functional properties to the antibody compounds disclosed herein involves randomly mutating amino acids within the grafted CDRs without changing the framework, and screening the resultant molecules for binding affinity and other functional properties that are as good as or better than those of the parent antibody compounds. Single mutations can also be introduced at each amino acid position within each CDR, followed by assessing the effects of such mutations on binding affinity and other functional properties. Single mutations producing improved properties can be combined to assess their effects in combination with one another.

Further, a combination of both of the foregoing approaches is possible. After CDR grafting, one can back-mutate specific framework regions in addition to introducing amino acid changes in the CDRs. This methodology is described in Wu et al. (1999) *J. Mol. Biol.* 294:151-162.

Applying the teachings of the present invention, a person skilled in the art can use common techniques, e.g., site-directed mutagenesis, to substitute amino acids within the presently disclosed CDR and framework sequences and thereby generate further variable region amino acid sequences derived from the present sequences. All alternative naturally occurring amino acids can be introduced at a specific substitution site. The methods disclosed herein can then be used to screen these additional variable region amino acid sequences to identify sequences having the indicated in vivo functions. In this way, further sequences suitable for preparing human engineered antibodies and antigen-binding portions thereof in accordance with the present invention can be identified. Preferably, amino acid substitution within the frameworks is restricted to one, two, or three positions within any one or more of the 4 light chain and/or heavy chain framework regions disclosed herein. Preferably, amino acid substitution within the CDRs is restricted to one, two, or three positions within any one or more of the 3 light chain and/or heavy chain CDRs. Combinations of the various changes within these framework regions and CDRs described above are also possible.

The term "treating" (or "treat" or "treatment") refers to processes involving a slowing, interrupting, arresting, controlling, stopping, reducing, or reversing the progression or severity of a symptom, disorder, condition, or disease, but does not necessarily involve a total elimination of all disease-related symptoms, conditions, or disorders associated with CGRP activity.

The term "migraine(s)" as used herein refers to "migraines without aura" (formerly "common migraine") and "migraines with aura" (formerly "classical migraines") according to the Headache Classification Committee of the International Headache Society (International Headache Society, 2004). For example, "migraines without aura", typically may be characterized as having a pulsating quality, a moderate or severe intensity, are aggravated by routine physical activity, are unilaterally located and are associated with nausea and with photophobia and phonophobia. "Migraines with aura" may include disturbances in vision, disturbances in other senses, unilateral weakness, and in some instances difficulty with speech.

The human engineered antibodies of the present invention can be used as medicaments in human medicine, administered by a variety of routes. Most preferably, such compositions are for parenteral administration. Such pharmaceutical compositions can be prepared by methods well known in the art (See, e.g., Remington: The Science and Practice of Pharmacy, 19$^{th}$ ed. (1995), A. Gennaro et al., Mack Publishing Co.) and comprise a human engineered antibody as disclosed herein, and a pharmaceutically acceptable carrier, diluent, or excipient.

The results of the following assays demonstrate that the exemplified monoclonal antibodies and antigen-binding fragments thereof of the present invention may be used for treating osteoarthritis pain.

EXAMPLE 1

Production of Antibodies

Antibodies I-V can be made and purified as follows. An appropriate host cell, such as HEK 293 EBNA or CHO, is either transiently or stably transfected with an expression system for secreting antibodies using an optimal predetermined HC:LC vector ratio or a single vector system encoding both LC, such as SEQ ID NO: 27, SEQ ID NO: 28, SEQ ID NO: 29, SEQ ID NO: 30, or SEQ ID NO: 31, and HC, such as SEQ ID NO: 32, SEQ ID NO: 33, SEQ ID NO: 34, SEQ ID NO: 35 or SEQ ID NO: 36. Clarified media, into which the antibody has been secreted, is purified using any of many commonly-used techniques. For example, the medium may be conveniently applied to a Protein A or G Sepharose FF column that has been equilibrated with a compatible buffer, such as phosphate buffered saline (pH 7.4). The column is washed to remove nonspecific binding components. The bound antibody is eluted, for example, by pH gradient (such as 0.1 M sodium phosphate buffer pH 6.8 to 0.1 M sodium citrate buffer pH 3.0). Antibody fractions are detected, such as by SDS-PAGE, and then are pooled. Further purification is optional, depending on the intended use. The antibody may be concentrated and/or sterile filtered using common techniques. Soluble aggregate and multimers may be effectively removed by common techniques, including size exclusion, hydrophobic interaction, ion exchange, or hydroxyapatite chromatography. The purity of the antibody after these chromatography steps is greater than 99%.

The product may be immediately frozen at −70° C. or may be lyophilized. The amino acid sequences for these exemplified antibodies are provided below.

TABLE 1

Antibody SEQ ID NOs

| Antibody | Heavy Chain | Light Chain | LCVR | HCVR |
|---|---|---|---|---|
| I | 32 | 27 | 17 | 22 |
| II | 33 | 28 | 18 | 23 |
| III | 34 | 29 | 19 | 24 |
| IV | 35 | 30 | 20 | 25 |
| V | 36 | 31 | 21 | 26 |

| Antibody | HCDR1 | HCDR2 | HCDR3 | LCDR1 | LCDR2 | LCDR3 |
|---|---|---|---|---|---|---|
| I | 12 | 13 | 14 | 3 | 4 | 5 |
| II | 12 | 15 | 14 | 3 | 4 | 5 |
| III | 12 | 16 | 39 | 6 | 7 | 5 |
| IV | 12 | 15 | 39 | 8 | 4 | 5 |
| V | 12 | 15 | 39 | 9 | 7 | 5 |

EXAMPLE 2

Affinity (Kd) Measurements for Human Engineered CGRP Antibodies

Binding affinity of the exemplified antibodies to CGRP is determined using a surface plasmon resonance assay on a Biacore T100 instrument primed with HBS-EP+(GE Healthcare, 10 mM Hepes pH7.4+150 mM NaCl+3 mM EDTA+ 0.05% surfactant P20) running buffer and analysis temperature set at 37° C. A CM5 chip containing immobilized protein A (generated using standard NHS-EDC amine coupling) on all four flow cells (Fc) is used to employ a capture methodology. Antibody samples are prepared at 2 μg/mL by dilution into running buffer. Human CGRP samples are prepared at final concentrations of 5.0, 2.5, 1.3, 0.63, 0.31, and 0 (blank) nM by dilution into running buffer. A fresh, single-use aliquot of CGRP is used for each replicate experiment to avoid multiple freeze-thaw cycles. Each analysis cycle consists of (1) capturing antibody samples on separate flow cells (Fc2, Fc3, and Fc4), (2) injection of 350 μL (210-sec) of CGRP over all Fc at 100 μL/min, (3) return to buffer flow for 10 min to monitor dissociation phase, (4) regeneration of chip surfaces with a 5 μL (15-sec) injection of glycine, pH1.5, (5) equilibration of chip surfaces with a 5 μL (15-sec) injection of HBS-EP+. Each CGRP concentration is injected in duplicate. Data are processed using standard double-referencing and fit to a 1:1 binding model using Biacore T100 Evaluation software, version 2.0.1, to determine the association rate ($k_{on}$, $M^{-1}s^{-1}$ units), dissociation rate ($k_{off}$, $s^{-1}$ units), and Rmax (RU units). The equilibrium dissociation constant ($K_D$) is calculated as from the relationship $K_D=k_{off}/k_{on}$, and is in molar units. Values provided in Table 2 are means of n number of experiments. Table 2 demonstrates that the exemplified antibodies of the present invention bind to CGRP with affinities <200 pM.

TABLE 2

Antibody Binding Affinities.

| Antibody | $K_D$ (pM) Mean ± SD | n |
|---|---|---|
| I | 190 | 1 |
| II | 26 ± 6 | 3 |

TABLE 2-continued

Antibody Binding Affinities.

| Antibody | $K_D$ (pM) Mean ± SD | n |
|---|---|---|
| III | 31 ± 19 | 6 |
| IV | 24 ± 10 | 4 |
| V | 24 ± 6 | 2 |

EXAMPLE 3

Reduction of Pain in an MIA Model

The injection of monoiodoacetic acid (MIA) into the knee joint of rats produces an acute inflammatory insult which then develops into chronic degeneration of the joint tissues in the injected joint. The pain resulting from the joint injury can be measured via differential weight bearing of the hind legs using an incapacitance tester. The MIA model has been well-described in the literature and has been used to demonstrate efficacy vs. pain for a variety of mechanisms and compounds. Efficacy is routinely measured by the ability of a compound to partially normalize weight distribution.

To determine the ability of the exemplified antibodies of the present invention to reduce pain, male Lewis rats (Harlan, Indianapolis, Ind.) of approximately eight weeks of age at the time of MIA injection are used. The rats are housed in groups of two or three per cage and maintained in a constant temperature and on a 12 hour light/12 hour dark cycle. Animals have free access to food and water at all times except during data collection. All experiments are carried out according to protocols approved by the Eli Lilly Institutional Animal Care and Use Committee.

The right knees of each rat are injected with 0.3 mg MIA in 50 μL of saline and the left knees with 50 μL of saline on day 0. On a set day post MIA, human IgG4 control or test CGRP antibody is subcutaneously administered in PBS (n=6 per group). Three days post dosing with test CGRP antibody, pain is measured using incapacitance testing which measures the difference in hind paw weight bearing between the MIA treated and saline injected knees. Each measurement is the average of three separate measurements each measured over 1 second.

Data are presented as percent inhibition of pain calculated by dividing the mean of the CGRP antibody treated group by the mean of the control antibody group, subtracting this value from 1 and multiplying this resulting value by 100. CGRP treated groups are also compared to vehicle groups by one way analysis of means and Dunnett's test using JMP (versions 5.1 and 6) statistical analysis program (SAS Institute Inc., Cary, N.C.). Differences are considered to be significant if the P value is less than 0.05. As shown in Table 3, the data demonstrate that the exemplified CGRP antibodies of the present invention significantly reduce pain.

TABLE 3

Percent Inhibition of MIA Induced Pain

| Antibody | Dose and route | MIA % inhibition | Significant by Dunnett's test (p < 0.05) |
|---|---|---|---|
| I | 20 mg/kg sc | 20% | Yes |
| II | 4 mg/kg sc | 30% | Yes |
| III | 4 mg/kg sc | 37% | Yes |
| IV | 4 mg/kg sc | 37% | Yes |
| V | 4 mg/kg sc | 19% | yes |

EXAMPLE 4

Inhibition of CGRP Induced cAMP Formation in SK-N-MC Cells

To compare the ability of an antibody of the present invention to Antibody G1 (LCVR—SEQ ID NO: 40 and HCVR—SEQ ID NO: 41), inhibition of CGRP induced cAMP formation in SK-N-MC is determined Binding of CGRP to its receptor results in the stimulation of cAMP production. The CGRP receptor is a hetero-trimeric complex consisting of the Calcitonin receptor-Like Receptor (CLR, a G-protein coupled receptor) and Receptor Activity Modifying Protein (RAMP)-1, coupled cytoplasmically to Receptor Component Protein (RCP). The human neuroepithelioma cell line SK-N-MC expresses these 3 molecules naturally and can therefore be used to assess the effect of CGRP on signal transduction events. Production of cAMP is a standard measure for G-protein coupled receptor activation.

SK-N-MC cells are cultured in MEM, containing 10% FBS, 1×MEM non-essential amino acids, 1×100 mM MEM Sodium Pyruvate, 1×Pen/Strep, and 2 mM L-glutamine. After harvesting, cells are washed once and resuspended in assay buffer (stimulation buffer (HBSS with Mg and Ca, 5 mM HEPES, 0.1% BSA, 100 uM Ascorbic acid) diluted 1:2 with Dulbecco's PBS containing a final concentration of 0.5 mM IBMX) and plated in 96-well plates at 15,000 cells per well. Test antibody or a control human IgG4 antibody are added (serial 4-fold dilutions in assay buffer, 10 concentrations) to the cells, followed by a fixed amount of human α-CGRP (2 nM; Bachem H1470). Plates are incubated for 1 hr at room temperature. Levels of cAMP are measured by a homogeneous time resolved fluorescence (HTRF) assay system (Cisbio).

The amount of cAMP induced by 2 nM human CGRP in the presence of varying concentrations of antibody is calculated as a percentage inhibition compared to CGRP alone. The antibody concentration producing 50% inhibition of cAMP production (IC50) is then calculated from a 4-parameter curve fit model. Following the procedures as described herein, Antibody III ($IC_{50}$ of 0.41 nM) inhibited the amount of CGRP induced cAMP to a much greater extent than Antibody G1 ($IC_{50}$ of 5.36 nM) possibly due to Antibody III's faster $K_{on}$ rate ($K_{on}$ rate as measured by Biacore)

EXAMPLE 5

Rat Dural Plasma Protein Extravasation (PPE) Model

The rat PPE model is a well established pre-clinical model that may be used to evaluate the efficacy of anti-CGRP antibodies for the treatment of migraine.

A 2 mg/mL solution of an anti-CGRP antibody (Ab) is prepared in saline solution. All subsequent dilutions are made with saline. A 2 mg/mL solution of monoclonal isotype control antibody (IgG) is also prepared in saline.

Male Sprague-Dawley rats from Harlan Laboratories (250 to 350 g) are anesthetized with Nembutal (60 mg/kg, ip.) and placed in a stereotaxic frame (David Kopf Instruments) with the incisor bar set at −2.5 mm Following a mid-line sagittal scalp incision, two pairs of bilateral holes are drilled through the skull (3.2 mm posteriorly, 1.8 and 3.8 mm laterally, all coordinates referenced to bregma). Pairs of stainless steel stimulating electrodes (Rhodes Medical Systems Inc), insulated except at the tips, are lowered through the holes in both hemispheres to a depth of 9.2 mm below the dura. Test antibodies or saline vehicle are administered intravenously via the femoral vein (1 mL/kg). Eight minutes later a solution of fluoroscein isothiocyanate (FITC) dye-labeled bovine serum albumin (BSA) (FITC-BSA, Sigma A9771) (20 mg/kg, iv.) is injected into the femoral vein to function as a marker for protein extravasation. Ten minutes following dosing with test antibodies or vehicle, the left trigeminal ganglion is stimulated for 5 minutes at a current intensity of 1.0 mA (5 Hz, 5 ms duration) with a Model S48 Grass Instrument Stimulator. Five minutes following stimulation, the rats are killed by exsanguination with 40 mL of saline. The exsanguination also rinses residual FITC/BSA out of the blood vessels. The top of the skull is removed to collect the dural membranes. The membrane samples are removed from both hemispheres, rinsed with water, and spread flat on microscope slides. The slides are dried for 15 minutes on a slide warmer and cover-slipped with a 70% glycerol/water solution.

A fluorescence microscope (Zeiss) equipped with a grating monochromator and a spectrophotometer are used to quantify the amount of FITC-BSA dye in each dural sample. The microscope is equipped with a motorized stage interfaced with a personal computer. This facilitates the computer-controlled movement of the stage, with fluorescence measurements at 25 points (500 μm steps) on each dural sample. The extravasation induced by electrical stimulation of the trigeminal ganglion is an ipsilateral effect (i.e. occurs only on the side of the dura in which the trigeminal ganglion is stimulated). This allows the other (unstimulated) half of the dura to be used as a control. The extravasation ratio (i.e. the ratio of the amount of extravasation in the dura from the stimulated side compared to the unstimulated side) is calculated.

| SEQUENCES | |
|---|---|
| | (SEQ ID NO: 1) |
| ACDTATCVTHRLAGLLSRSGGVVKNNFVPTNVGSKAF | |
| | (SEQ ID NO: 2) |
| ACNTATCVTHRLAGLLSRSGGMVKSNFVPTNVGSKAF | |

| Antibody | LCDR1 | LCDR2 | LCDR3 |
|---|---|---|---|
| I | RASQDID NYLN (SEQ ID NO: 3) | YTSEYHS (SEQ ID NO: 4) | QQGDALP PT (SEQ ID NO: 5) |
| II | RASQDID NYLN (SEQ ID NO: 3) | YTSEYHS (SEQ ID NO: 4) | QQGDALP PT (SEQ ID NO: 5) |
| III | RASKDIS KYLN (SEQ ID NO: 6) | YTSGYHS (SEQ ID NO: 7) | QQGDALP PT (SEQ ID NO: 5) |
| IV | RASRPID KYLN (SEQ ID NO: 8) | YTSEYHS (SEQ ID NO: 4) | QQGDALP PT (SEQ ID NO: 5) |
| V | RASQDID KYLN (SEQ ID NO: 9) | YTSGYHS (SEQ ID NO: 7) | QQGDALP PT (SEQ ID NO: 5) |
| consensus | RASX$_1$X$_2$I X$_3$X$_4$YLN (SEQ ID NO: 10) | YTSX$_5$YHS (SEQ ID NO: 11) | QQGDALP PT (SEQ ID NO: 5) |

$X_1$ is Q, R or K;
$X_2$ is D or P;
$X_3$ is D or S;
$X_4$ is N or K;
and
$X_5$ is G or E.

| Antibody | HCDR1 | HCDR2 | HCDR3 |
|---|---|---|---|
| I | GYTFGNY WMQ (SEQ ID NO: 12) | AIYEGTGDT RYIQKFAG (SEQ ID NO: 13) | LSDYVSG FSY (SEQ ID NO: 14) |
| II | GYTFGNY WMQ (SEQ ID NO: 12) | AIYEGTGKT VYIQKFAG (SEQ ID NO: 15) | LSDYVSG FSY (SEQ ID NO: 14) |
| III | GYTFGNY WMQ (SEQ ID NO: 12) | AIYEGTGKT VYIQKFAD (SEQ ID NO: 16) | LSDYVSG FGY (SEQ ID NO: 39) |
| IV | GYTFGNY WMQ (SEQ ID NO: 12) | AIYEGTGKT VYIQKFAG (SEQ ID NO: 15) | LSDYVSG FGY (SEQ ID NO: 39) |
| V | GYTFGNY WMQ (SEQ ID NO: 12) | AIYEGTGKT VYIQKFAG (SEQ ID NO: 15) | LSDYVSG FGY (SEQ ID NO: 39) |
| consensus | GYTFGNY WMQ (SEQ ID NO: 12) | AIYEGTGX$_6$T X$_7$YIQKFAX$_8$ (SEQ ID NO: 37) | LSDYVSG FX$_9$Y (SEQ ID NO: 38) |

$X_6$ is K or D;
$X_7$ is V or R;
$X_8$ is D or G;
and
$X_9$ is G or S.

(SEQ ID NO: 17)
DIQMTQSPSSLSASVGDRVTITCRASQDIDNYLNWYQQKPGKAP
KLLIYYTSEYHSGVPSRFSGSGSGTDFTFTISSLQPEDIATYYC
QQGDALPPTFGQGTKLEIK (SEQ ID NO: 18)
DIQMTQSPSSLSASVGDRVTITCRASQDIDNYLNWYQQKPGKAP
KLLIYYTSEYHSGVPSRFSGSGSGTDFTFTISSLQPEDIATYYC
QQGDALPPTFGQGTKLEIK (SEQ ID NO: 19)
DIQMTQSPSSLSASVGDRVTITCRASKDISKYLNWYQQKPGKAP
KLLIYYTSGYHSGVPSRFSGSGSGTDFTLTISSLQPEDFATYYC
QQGDALPPTFGGGTKVEIK (SEQ ID NO: 20)
DIQMTQSPSSLSASVGDRVTITCRASRPIDKYLNWYQQKPGKAP
KLLIYYTSEYHSGVPSRFSGSGSGTDFTFTISSLQPEDIATYYC
QQGDALPPTFGQGTKLEIK (SEQ ID NO: 21)
DIQMTQSPSSLSASVGDRVTITCRASQDIDKYLNWYQQKPGKAP
KLLIYYTSGYHSGVPSRFSGSGSGTDFTLTISSLQPEDFATYYC
QQGDALPPTFGGGTKVEIK (SEQ ID NO: 22)
QVQLVQSGAEVKKPGASVKVSCKASGYTFGNYWMQWVRQAPGQG
LEWMGAIYEGTGDTRYIQKFAGRVTMTRDTSTSTVYMELSSLRS
EDTAVYYCARLSDYVSGFSYWGQGTLVTVSS (SEQ ID NO: 23)
QVQLVQSGAEVKKPGASVKVSCKASGYTFGNYWMQWVRQAPGQG
LEWMGAIYEGTGKTVYIQKFAGRVTMTRDTSTSTVYMELSSLRS
EDTAVYYCARLSDYVSGFSYWGQGTLVTVSS (SEQ ID NO: 24)
QVQLVQSGAEVKKPGSSVKVSCKASGYTFGNYWMQWVRQAPGQG
LEWMGAIYEGTGKTVYIQKFADRVTITADKSTSTAYMELSSLRS
EDTAVYYCARLSDYVSGFGYWGQGTTVTVSS (SEQ ID NO: 25)
QVQLVQSGAEVKKPGASVKVSCKASGYTFGNYWMQWVRQAPGQG
LEWMGAIYEGTGKTVYIQKFAGRVTMTRDTSTSTVYMELSSLRS
EDTAVYYCARLSDYVSGFGYWGQGTLVTVSS (SEQ ID NO: 26)
QVQLVQSGAEVKKPGSSVKVSCKASGYTFGNYWMQWVRQAPGQG
LEWMGAIYEGTGKTVYIQKFAGRVTITADKSTSTAYMELSSLRS
EDTAVYYCARLSDYVSGFGYWGQGTTVTVSS (SEQ ID NO: 27)
DIQMTQSPSSLSASVGDRVTITCRASQDIDNYLNWYQQKPGKAP
KLLIYYTSEYHSGYPSRFSGSGSGTDFTFTISSLQPEDIATYYC
QQGDALPPTFGQGTKLEIKRTVAAPSVFIFPPSDEQLKSGTASV
VCLLNNFYPREAKVQWKVDNALQSGNSQESVTEQDSKDSTYSLS
STLTLSKADYEKHKVYACEVTHQGLSSPVTKSFNRGEC (SEQ ID NO: 28)
DIQMTQSPSSLSASVGDRVTITCRASQDIDNYLNWYQQKPGKAP
KLLIYYTSEYHSGYPSRFSGSGSGTDFTFTISSLQPEDIATYYC
QQGDALPPTFGQGTKLEIKRTVAAPSVFIFPPSDEQLKSGTASV
VCLLNNFYPREAKVQWKVDNALQSGNSQESVTEQDSKDSTYSLS
STLTLSKADYEKHKVYACEVTHQGLSSPVTKSFNRGEC (SEQ ID NO: 29)
DIQMTQSPSSLSASVGDRVTITCRASKDISKYLNWYQQKPGKAP
KLLIYYTSGYHSGYPSRFSGSGSGTDFTLTISSLQPEDFATYYC
QQGDALPPTFGGGTKVEIKRTVAAPSVFIFPPSDEQLKSGTASV
VCLLNNFYPREAKVQWKVDNALQSGNSQESVTEQDSKDSTYSLS
STLTLSKADYEKHKVYACEVTHQGLSSPVTKSFNRGEC (SEQ ID NO: 30)
DIQMTQSPSSLSASVGDRVTITCRASRPIDKYLNWYQQKPGKAP
KLLIYYTSEYHSGVPSRFSGSGSGTDFTFTISSLQPEDIATYYC
QQGDALPPTFGQGTKLEIKRTVAAPSVFIFPPSDEQLKSGTASV
VCLLNNFYPREAKVQWKVDNALQSGNSQESVTEQDSKDSTYSLS
STLTLSKADYEKHKVYACEVTHQGLSSPVTKSFNRGEC (SEQ ID NO: 31)
DIQMTQSPSSLSASVGDRVTITCRASQDIDKYLNWYQQKPGKAP
KLLIYYTSGYHSGYPSRFSGSGSGTDFTLTISSLQPEDFATYYC
QQGDALPPTFGGGTKVEIKRTVAAPSVFIFPPSDEQLKSGTASV
VCLLNNFYPREAKVQWKVDNALQSGNSQESVTEQDSKDSTYSLS
STLTLSKADYEKHKVYACEVTHQGLSSPVTKSFNRGEC (SEQ ID NO: 32)
QVQLVQSGAEVKKPGASVKVSCKASGYTFGNYWMQWVRQAPGQG
LEWMGAIYEGTGDTRYIQKFAGRVTMTRDTSTSTVYMELSSLRS
EDTAVYYCARLSDYVSGFSYWGQGTLVTVSSASTKGPSVFPLAP
CSRSTSESTAALGCLVKDYFPEPVTVSWNSGALTSGVHTFPAVL
QSSGLYSLSSVVTVPSSSLGTKTYTCNVDHKPSNTKVDKRVESK
YGPPCPPCPAPEAAGGPSVFLFPPKPKDTLMISRTPEVTCVVVD
VSQEDPEVQFNWYVDGVEVHNAKTKPREEQFNSTYRVVSVLTVL
HQDWLNGKEYKCKVSNKGLPSSIEKTISKAKGQPREPQVYTLPP
SQEEMTKNQVSLTCLVKGFYPSDIAVEWESNGQPENNYKTTPPV
LDSDGSFFLYSRLTVDKSRWQEGNVFSCSVMHEALHNHYTQKSL
SLSLG (SEQ ID NO: 33)
QVQLVQSGAEVKKPGASVKVSCKASGYTFGNYWMQWVRQAPGQG
LEWMGAIYEGTGKTVYIQKFAGRVTMTRDTSTSTVYMELSSLRS
EDTAVYYCARLSDYVSGFSYWGQGTLVTVSSASTKGPSVFPLAP
CSRSTSESTAALGCLVKDYFPEPVTVSWNSGALTSGVHTFPAVL
QSSGLYSLSSVVTVPSSSLGTKTYTCNVDHKPSNTKVDKRVESK
YGPPCPPCPAPEAAGGPSVFLFPPKPKDTLMISRTPEVTCVVVD
VSQEDPEVQFNWYVDGVEVHNAKTKPREEQFNSTYRVVSVLTVL
HQDWLNGKEYKCKVSNKGLPSSIEKTISKAKGQPREPQVYTLPP
SQEEMTKNQVSLTCLVKGFYPSDIAVEWESNGQPENNYKTTPPV
LDSDGSFFLYSRLTVDKSRWQEGNVFSCSVMHEALHNHYTQKSL
SLSLG (SEQ ID NO: 34)
QVQLVQSGAEVKKPGSSVKVSCKASGYTFGNYWMQWVRQAPGQG
LEWMGAIYEGTGKTVYIQKFADRVTITADKSTSTAYMELSSLRS
EDTAVYYCARLSDYVSGFGYWGQGTTVTVSSASTKGPSVFPLAP
CSRSTSESTAALGCLVKDYFPEPVTVSWNSGALTSGVHTFPAVL
QSSGLYSLSSVVTVPSSSLGTKTYTCNVDHKPSNTKVDKRVESK
YGPPCPPCPAPEAAGGPSVFLFPPKPKDTLMISRTPEVTCVVVD
VSQEDPEVQFNWYVDGVEVHNAKTKPREEQFNSTYRVVSVLTVL
HQDWLNGKEYKCKVSNKGLPSSIEKTISKAKGQPREPQVYTLPP
SQEEMTKNQVSLTCLVKGFYPSDIAVEWESNGQPENNYKTTPPV
LDSDGSFFLYSRLTVDKSRWQEGNVFSCSVMHEALHNHYTQKSL
SLSLG (SEQ ID NO: 35)
QVQLVQSGAEVKKPGASVKVSCKASGYTFGNYWMQWVRQAPGQG
LEWMGAIYEGTGKTVYIQKFAGRVTMTRDTSTSTVYMELSSLRS
EDTAVYYCARLSDYVSGFGYWGQGTLVTVSSASTKGPSVFPLAP
CSRSTSESTAALGCLVKDYFPEPVTVSWNSGALTSGVHTFPAVL
QSSGLYSLSSVVTVPSSSLGTKTYTCNVDHKPSNTKVDKRVESK
YGPPCPPCPAPEAAGGPSVFLFPPKPKDTLMISRTPEVTCVVVD
VSQEDPEVQFNWYVDGVEVHNAKTKPREEQFNSTYRVVSVLTVL
HQDWLNGKEYKCKVSNKGLPSSIEKTISKAKGQPREPQVYTLPP
SQEEMTKNQVSLTCLVKGFYPSDIAVEWESNGQPENNYKTTPPV
LDSDGSFFLYSRLTVDKSRWQEGNVFSCSVMHEALHNHYTQKSL
SLSLG (SEQ ID NO: 36)
QVQLVQSGAEVKKPGSSVKVSCKASGYTFGNYWMQWVRQAPGQG
LEWMGAIYEGTGKTVYIQKFAGRVTITADKSTSTAYMELSSLRS
EDTAVYYCARLSDYVSGFGYWGQGTTVTVSSASTKGPSVFPLAP
CSRSTSESTAALGCLVKDYFPEPVTVSWNSGALTSGVHTFPAVL
QSSGLYSLSSVVTVPSSSLGTKTYTCNVDHKPSNTKVDKRVESK
YGPPCPPCPAPEAAGGPSVFLFPPKPKDTLMISRTPEVTCVVVD
VSQEDPEVQFNWYVDGVEVHNAKTKPREEQFNSTYRVVSVLTVL
HQDWLNGKEYKCKVSNKGLPSSIEKTISKAKGQPREPQVYTLPP
SQEEMTKNQVSLTCLVKGFYPSDIAVEWESNGQPENNYKTTPPV
LDSDGSFFLYSRLTVDKSRWQEGNVFSCSVMHEALHNHYTQKSL
SLSLG (SEQ ID NO: 40)
EIVLTQSPATLSLSPGERATLSCKASKRVTTYVSWYQQKPGQAP
RLLIYGASNRYLGIPARFSGSGSGTDFTLTISSLEPEDFAVYYC
SQSYNYPYTFGQGTKLEIK (SEQ ID NO: 41)
EVQLVESGGGLVQPGGSLRLSCAASGFTFSNYWISWVRQAPGKG
LEWVAEIRSESDASATHYAEAVKGRFTISRDNAKNSLYLQMNSL
RAEDTAVYYCLAYFDYGLAIQNYWGQGTLVTVSS

| SEQUENCES |
|---|
| (SEQ ID NO: 42)<br>DIQMTQSPSSLSASVGDRVTITCRASX$_1$X$_2$IX$_3$X$_4$YLNWYQQKPG<br>KAPKLLIYYTSX$_5$YHSGVPSRFSGSGSGTDFTX$_6$TISSLQPEDX$_7$<br>ATYYCQQGDALPPTFGX$_8$GTKX$_9$EIK |

$X_1$ = Q, K, or R;
$X_2$ = D or P;
$X_3$ D or S;
$X_4$ = K or N;
$X_5$ = E or G;
$X_6$ = F or L;
$X_7$ = I or F;
$X_8$ = Q or G;
and
$X_9$ = L or V.

| SEQUENCES |
|---|
| (SEQ ID NO: 43)<br>QVQLVQSGAEVKKPGX$_1$SVKVSCKASGYTFGNYWMQWVRQAPGQ<br>GLEWMGAIYEGTGX$_2$TX$_3$YIQKFAX$_4$RVTX$_5$TX$_6$DX$_7$STSTX$_8$YME<br>LSSLRSEDTAVYYCARLSDYVSGFX$_9$YWGQGTX$_{10}$VTVSS |

$X_1$ = A or S;
$X_2$ = K or D;
$X_3$ = V or R;
$X_4$ = G or D;
$X_5$ = M or I;
$X_6$ = R or A;
$X_7$ = T or K;
$X_8$ = V or A;
$X_9$ = G or S;
and
$X_{10}$ = L or T.

We claim:

1. A method of treating migraines comprising administering to a human patient in need thereof a human engineered calcitonin gene related peptide (CGRP) antibody comprising a light chain variable region (LCVR) and a heavy chain variable region (HCVR), wherein the amino acid sequence of said LCVR and HCVR is selected from the group consisting of:
   a. LCVR of SEQ ID NO: 17 and HCVR of SEQ ID NO: 22;
   b. LCVR of SEQ ID NO: 18 and HCVR of SEQ ID NO: 23;
   c. LCVR of SEQ ID NO: 19 and HCVR of SEQ ID NO: 24;
   d. LCVR of SEQ ID NO: 20 and HCVR of SEQ ID NO: 25; and
   e. LCVR of SEQ ID NO: 21 and HCVR of SEQ ID NO: 26.

2. The method according to claim 1 wherein the LCVR amino acid sequence is SEQ ID NO: 19 and the HCVR amino acid sequence is SEQ ID NO: 24.

3. A method of treating migraines comprising administering to a human patient in need thereof a human engineered CGRP antibody comprising a light chain (LC) and a heavy chain (HC), wherein the amino acid sequence of said LC and HC is selected from the group consisting of:
   a. Light chain of SEQ ID NO: 27 and heavy chain of SEQ ID NO: 32;
   b. Light chain of SEQ ID NO: 28 and heavy chain of SEQ ID NO: 33;
   c. Light chain of SEQ ID NO: 29 and heavy chain of SEQ ID NO: 34;
   d. Light chain of SEQ ID NO: 30 and heavy chain of SEQ ID NO: 35; and
   e. Light chain of SEQ ID NO: 31 and heavy chain of SEQ ID NO: 36.

4. The method according to claim 3 wherein the LC amino acid sequence is SEQ ID NO: 29 and the HC amino acid sequence is SEQ ID NO: 34.

5. A method of treating migraines comprising administering to a human patient in need thereof a human engineered CGRP antibody comprising two light chains (LC) and two heavy chains (HC), wherein the amino acid sequence of said LC and HC is selected from the group consisting of:
   a. Light chain of SEQ ID NO: 27 and heavy chain of SEQ ID NO: 32;
   b. Light chain of SEQ ID NO: 28 and heavy chain of SEQ ID NO: 33;
   c. Light chain of SEQ ID NO: 29 and heavy chain of SEQ ID NO: 34;
   d. Light chain of SEQ ID NO: 30 and heavy chain of SEQ ID NO: 35; and
   e. Light chain of SEQ ID NO: 31 and heavy chain of SEQ ID NO: 36.

6. The method according to claim 5 wherein the LC amino acid sequence is SEQ ID NO: 29 and the HC amino acid sequence is SEQ ID NO: 34.

7. A method of treating migraines comprising administering to a human patient a pharmaceutical composition comprising a human engineered CGRP antibody, wherein the human engineered CGRP antibody comprises two light chain amino acid sequences of SEQ ID NO: 29 and two heavy chain amino acid sequences of SEQ ID NO: 34.

* * * * *

UNITED STATES PATENT AND TRADEMARK OFFICE

(12)         CERTIFICATE EXTENDING PATENT TERM
UNDER 35 U.S.C. § 156

| | | | |
|---|---|---|---|
| (68) | PATENT NO. | : | 9,505,838 |
| (45) | ISSUED | : | November 29, 2016 |
| (75) | INVENTOR | : | Allan et al. |
| (73) | PATENT OWNER | : | Eli Lilly and Company |
| (95) | PRODUCT | : | EMGALITY® (galcanezumab-gnlm) |

This is to certify that an application under 35 U.S.C. § 156 has been filed in the United States Patent and Trademark Office, requesting extension of the term of U.S. Patent No. 9,505,838 based upon the regulatory review of the product EMGALITY® (galcanezumab-gnlm) by the Food and Drug Administration. According to United States Patent and Trademark Office records, the original expiration date of the patent as of the date of issuance of this certificate is August 21, 2031. Because it appears that the requirements of the law have been met, this certificate extends the term of the patent for the period of

(94)                                       403 days subject to the payment of maintenance fees as provided by law, with all rights pertaining thereto as provided by 35 U.S.C. § 156.

I have caused the seal of the United States Patent and Trademark Office to be affixed this 18th day of November 2025.

John A. Squires
Under Secretary of Commerce for Intellectual Property and
Director of the United States Patent and Trademark Office